US009214150B2

(12) United States Patent
Kwatra

(10) Patent No.: US 9,214,150 B2
(45) Date of Patent: Dec. 15, 2015

(54) CONTINUOUS ADAPTATION OF SECONDARY PATH ADAPTIVE RESPONSE IN NOISE-CANCELING PERSONAL AUDIO DEVICES

(75) Inventor: Nitin Kwatra, Austin, TX (US)

(73) Assignee: CIRRUS LOGIC, INC., Austin, TX (US)

( * ) Notice: Subject to any disclaimer, the term of this patent is extended or adjusted under 35 U.S.C. 154(b) by 637 days.

(21) Appl. No.: 13/458,585

(22) Filed: Apr. 27, 2012

(65) Prior Publication Data

US 2012/0308027 A1 Dec. 6, 2012

Related U.S. Application Data

(60) Provisional application No. 61/493,162, filed on Jun. 3, 2011.

(51) Int. Cl.
*A61F 11/06* (2006.01)
*G10K 11/178* (2006.01)

(52) U.S. Cl.
CPC ...... *G10K 11/1784* (2013.01); *G10K 2210/108* (2013.01); *G10K 2210/3049* (2013.01)

(58) Field of Classification Search
CPC ............................................ G10K 2210/3049
See application file for complete search history.

(56) References Cited

U.S. PATENT DOCUMENTS 5,251,263 A 10/1993 Andrea et al.
5,278,913 A 1/1994 Delfosse et al.
5,321,759 A 6/1994 Yuan
5,337,365 A 8/1994 Hamabe et al.
5,359,662 A 10/1994 Yuan et al.
5,410,605 A 4/1995 Sawada et al.

(Continued)

FOREIGN PATENT DOCUMENTS

DE 102011013343 A1 9/2012
EP 1880699 A2 1/2008

(Continued)

OTHER PUBLICATIONS

U.S. Appl. No. 13/686,353, filed Nov. 27, 2012, Hendrix, et al.

(Continued)

*Primary Examiner* — Joseph Saunders, Jr.
*Assistant Examiner* — James Mooney
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that adaptively generates an anti-noise signal from a reference microphone signal and injects the anti-noise signal into the speaker or other transducer output to cause cancellation of ambient audio sounds. An error microphone is also provided proximate the speaker to provide an error signal indicative of the effectiveness of the noise cancellation. A secondary path estimating adaptive filter is used to estimate the electro-acoustical path from the noise canceling circuit through the transducer so that source audio can be removed from the error signal. Noise is injected either continuously and inaudibly below the source audio, or in response to detection that the source audio is low in amplitude, so that the adaptation of the secondary path estimating adaptive filter can be maintained, irrespective of the presence and amplitude of the source audio.

24 Claims, 4 Drawing Sheets

(56) References Cited

U.S. PATENT DOCUMENTS 5,425,105 A 6/1995 Lo et al.
5,445,517 A 8/1995 Kondou et al.
5,465,413 A 11/1995 Enge et al.
5,548,681 A 8/1996 Gleaves et al.
5,586,190 A 12/1996 Trantow et al.
5,640,450 A 6/1997 Watanabe
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,946,391 A 8/1999 Dragwidge et al.
5,991,418 A 11/1999 Kuo
6,041,126 A 3/2000 Terai et al.
6,118,878 A 9/2000 Jones
6,219,427 B1 4/2001 Kates et al.
6,278,786 B1 8/2001 McIntosh
6,282,176 B1 8/2001 Hemkumar
6,418,228 B1 7/2002 Terai et al.
6,434,246 B1 8/2002 Kates et al.
6,434,247 B1 8/2002 Kates et al.
6,522,746 B1 2/2003 Marchok et al.
6,683,960 B1 1/2004 Fujii et al.
6,766,292 B1 7/2004 Chandran
6,768,795 B2 7/2004 Feltstrom et al.
6,850,617 B1 2/2005 Weigand
6,940,982 B1 9/2005 Watkins
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,680,456 B2 3/2010 Muhammad et al.
7,742,790 B2 6/2010 Konchitsky et al.
7,817,808 B2 10/2010 Konchitsky et al.
8,019,050 B2 9/2011 Mactavish et al.
8,249,262 B2 8/2012 Chua et al.
8,290,537 B2 10/2012 Lee et al.
8,325,934 B2 12/2012 Kuo
8,379,884 B2 2/2013 Horibe et al.
8,401,200 B2 3/2013 Tiscareno et al.
8,442,251 B2 5/2013 Jensen et al.
8,804,974 B1 8/2014 Melanson
8,908,877 B2 12/2014 Abdollahzadeh Milani et al.
2001/0053228 A1 12/2001 Jones
2002/0003887 A1* 1/2002 Zhang et al. ................. 381/71.1
2003/0063759 A1 4/2003 Brennan et al.
2003/0072439 A1 4/2003 Gupta
2003/0185403 A1 10/2003 Sibbald
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0035593 A1 2/2006 Leeds
2006/0055910 A1 3/2006 Lee
2006/0069556 A1 3/2006 Nadjar et al.
2006/0153400 A1 7/2006 Fujita et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0177532 A1 7/2008 Greiss et al.
2008/0181422 A1* 7/2008 Christoph .................... 381/73.1
2008/0226098 A1 9/2008 Haulick et al.
2008/0240413 A1 10/2008 Mohammad et al.
2008/0240455 A1 10/2008 Inoue et al.
2008/0240457 A1 10/2008 Inoue et al.
2009/0012783 A1 1/2009 Klein
2009/0034748 A1* 2/2009 Sibbald ........................ 381/71.6
2009/0041260 A1 2/2009 Jorgensen et al.
2009/0046867 A1 2/2009 Clemow
2009/0060222 A1 3/2009 Jeong et al.
2009/0080670 A1 3/2009 Solbeck et al.
2009/0086990 A1 4/2009 Christoph
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.
2009/0311979 A1 12/2009 Husted et al.
2010/0014683 A1 1/2010 Maeda et al.
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0098265 A1 4/2010 Pan et al.
2010/0124336 A1 5/2010 Shridhar et al.
2010/0124337 A1 5/2010 Wertz et al.
2010/0131269 A1 5/2010 Park et al.
2010/0142715 A1 6/2010 Goldstein et al.
2010/0150367 A1 6/2010 Mizuno
2010/0158330 A1 6/2010 Guissin et al.
2010/0166203 A1 7/2010 Peissig et al.
2010/0195838 A1 8/2010 Bright
2010/0195844 A1 8/2010 Christoph et al.
2010/0207317 A1 8/2010 Iwami et al.
2010/0246855 A1 9/2010 Chen
2010/0266137 A1 10/2010 Sibbald et al.
2010/0272276 A1 10/2010 Carreras et al.
2010/0272283 A1 10/2010 Carreras et al.
2010/0274564 A1 10/2010 Bakalos et al.
2010/0284546 A1 11/2010 DeBrunner et al.
2010/0291891 A1 11/2010 Ridgers et al.
2010/0296666 A1 11/2010 Lin
2010/0296668 A1 11/2010 Lee et al.
2010/0310086 A1 12/2010 Magrath et al.
2010/0322430 A1 12/2010 Isberg
2011/0007907 A1 1/2011 Park et al.
2011/0106533 A1 5/2011 Yu
2011/0129098 A1 6/2011 Delano et al.
2011/0130176 A1 6/2011 Magrath et al.
2011/0142247 A1 6/2011 Fellers et al.
2011/0144984 A1 6/2011 Konchitsky
2011/0158419 A1 6/2011 Theverapperuma et al.
2011/0206214 A1 8/2011 Christoph et al.
2011/0222698 A1 9/2011 Asao et al.
2011/0249826 A1 10/2011 Van Leest
2011/0288860 A1 11/2011 Schevciw et al.
2011/0293103 A1 12/2011 Park et al.
2011/0299695 A1 12/2011 Nicholson
2011/0305347 A1 12/2011 Wurm
2011/0317848 A1 12/2011 Ivanov et al.
2012/0135787 A1 5/2012 Kusunoki et al.
2012/0140917 A1 6/2012 Nicholson et al.
2012/0140942 A1 6/2012 Loeda
2012/0140943 A1 6/2012 Hendrix et al.
2012/0148062 A1 6/2012 Scarlett et al.
2012/0155666 A1 6/2012 Nair
2012/0170766 A1 7/2012 Alves et al.
2012/0207317 A1 8/2012 Abdollahzadeh Milani et al.

(56) References Cited

U.S. PATENT DOCUMENTS

| | | | |
|---|---|---|---|
| 2012/0215519 | A1 | 8/2012 | Park et al. |
| 2012/0250873 | A1 | 10/2012 | Bakalos et al. |
| 2012/0259626 | A1 | 10/2012 | Li et al. |
| 2012/0263317 | A1 | 10/2012 | Shin et al. |
| 2012/0300958 | A1 | 11/2012 | Klemmensen |
| 2012/0300960 | A1 | 11/2012 | Mackay et al. |
| 2012/0308021 | A1 | 12/2012 | Kwatra et al. |
| 2012/0308024 | A1 | 12/2012 | Alderson et al. |
| 2012/0308025 | A1 | 12/2012 | Hendrix et al. |
| 2012/0308026 | A1 | 12/2012 | Kamath et al. |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0083939 | A1 | 4/2013 | Fellers et al. |
| 2013/0243198 | A1 | 9/2013 | Van Rumpt |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0072134 | A1 | 3/2014 | Po et al. |
| 2014/0086425 | A1 | 3/2014 | Jensen et al. |
| 2014/0177851 | A1 | 6/2014 | Kitazawa et al. |
| 2014/0211953 | A1 | 7/2014 | Alderson et al. |
| 2014/0270222 | A1 | 9/2014 | Hendrix et al. |
| 2014/0270223 | A1 | 9/2014 | Li et al. |
| 2014/0270224 | A1 | 9/2014 | Zhou et al. |
| 2015/0092953 | A1 | 4/2015 | Abdollahzadeh Milani et al. |

FOREIGN PATENT DOCUMENTS

| | | | |
|---|---|---|---|
| EP | 1947642 | A1 | 7/2008 |
| EP | 2133866 | A1 | 12/2009 |
| EP | 2216774 | A1 | 8/2010 |
| EP | 2237573 | A1 | 10/2010 |
| EP | 2395500 | A1 | 12/2011 |
| EP | 2395501 | A1 | 12/2011 |
| GB | 2401744 | A | 11/2004 |
| GB | 2455821 | A | 6/2009 |
| GB | 2455824 | A | 6/2009 |
| GB | 2455828 | A | 6/2009 |
| GB | 2484722 | A | 4/2012 |
| JP | H06-186985 | A | 7/1994 |
| WO | WO 9911045 | | 3/1999 |
| WO | WO 03/015074 | A1 | 2/2003 |
| WO | WO 03015275 | A1 | 2/2003 |
| WO | WO 2004009007 | A1 | 1/2004 |
| WO | WO 2004017303 | A1 | 2/2004 |
| WO | WO 2007007916 | A1 | 1/2007 |
| WO | WO 2007113487 | A1 | 11/2007 |
| WO | WO 2010117714 | A1 | 10/2010 |
| WO | WO 2012134874 | A1 | 10/2012 |
| WO | WO 2015038255 | A1 | 3/2015 |

OTHER PUBLICATIONS

U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.
Parkins, et al., "Narrowband and broadband active control in an enclosure using the acoustic energy density", J. Acoust. Soc. Am. Jul. 2000, pp. 192-203, vol. 108, issue 1, US.
Feng, et al.., "A broadband self-tuning active noise equaliser", Signal Processing, Oct. 1, 1997, pp. 251-256, vol. 62, No. 2, Elsevier Science Publishers B.V. Amsterdam, NL.

(56) References Cited

OTHER PUBLICATIONS

Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
International Search Report and Written Opinion in PCT/US2012/039336, mailed on Apr. 12, 2013, 14 pages (pp. 1-14 in pdf).
Written Opinion of the International Preliminary Examining Authority in PCT/US2012/039336, mailed on Sep. 24, 2013, 5 pages (pp. 1-5 in pdf).
International Preliminary Report on Patentability in PCT/US2012/039336, mailed on Jan. 10, 2014, 24 pages (pp. 1-24 in pdf).
U.S. Appl. No. 14/029,159, filed Sep. 17, 2013, Li, et al.
U.S. Appl. No. 14/062,951, filed Oct. 25, 2013, Zhou, et al.
U.S. Appl. No. 13/968,007, filed Aug. 15, 2013, Hendrix, et al.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
U.S. Appl. No. 14/197,814, filed Mar. 5, 2014, Kaller, et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and The Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
U.S. Appl. No. 14/578,567, filed Dec. 22, 2014, Kwatra, et al.
Widrow, B., et al., Adaptive Noise Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
U.S. Appl. No. 14/656,124, filed Mar. 12, 2015, Hendrix, et al.
U.S. Appl. No. 14/734,321, filed Jun. 9, 2015, Alderson, et al.

* cited by examiner

CONTINUOUS ADAPTATION OF SECONDARY PATH ADAPTIVE RESPONSE IN NOISE-CANCELING PERSONAL AUDIO DEVICES

This U.S. Patent Application Claims priority under 35 U.S.C. 119(e) to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include adaptive noise cancellation (ANC), and more specifically, to control of ANC in a personal audio device that uses injected noise to provide continued adaptation of a secondary path estimate when source audio is absent or low in amplitude.

2. Background of the Invention

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Noise canceling operation can be improved by measuring the transducer output of a device at the transducer to determine the effectiveness of the noise canceling using an error microphone. The measured output of the transducer is ideally the source audio, e.g., downlink audio in a telephone and/or playback audio in either a dedicated audio player or a telephone, since the noise canceling signal(s) are ideally canceled by the ambient noise at the location of the transducer. To remove the source audio from the error microphone signal, the secondary path from the transducer through the error microphone can be estimated and used to filter the source audio to the correct phase and amplitude for subtraction from the error microphone signal. However, when source audio is absent, the secondary path estimate cannot typically be updated.

Therefore, it would be desirable to provide a personal audio device, including wireless telephones, that provides noise cancellation using a secondary path estimate to measure the output of the transducer and that can continuously adapt the secondary path estimate independent of whether source audio of sufficient amplitude is present.

SUMMARY OF THE INVENTION

The above stated objective of providing a personal audio device providing noise cancelling including a secondary path estimate that can be adapted continuously whether or not source audio of sufficient amplitude is present, is accomplished in a personal audio device, a method of operation, and an integrated circuit.

The personal audio device includes a housing, with a transducer mounted on the housing for reproducing an audio signal that includes both source audio for providing to a listener and an anti-noise signal for countering the effects of ambient audio sounds in an acoustic output of the transducer. A reference microphone is mounted on the housing to provide a reference microphone signal indicative of the ambient audio sounds. The personal audio device further includes an adaptive noise-canceling (ANC) processing circuit within the housing for adaptively generating an anti-noise signal from the reference microphone signal such that the anti-noise signal causes substantial cancellation of the ambient audio sounds. An error microphone is included for controlling the adaptation of the anti-noise signal to cancel the ambient audio sounds and for correcting for the electro-acoustical path from the output of the processing circuit through the transducer. The ANC processing circuit injects noise at a level sufficiently below the source audio level to be unnoticeable, either continuously, or at least when the source audio, e.g., downlink audio in telephones and/or playback audio in media players or telephones, is at such a low level that the secondary path estimating adaptive filter cannot properly continue adaptation.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates a signal that is injected into the speaker (or other transducer) output to cancel ambient acoustic events. A reference microphone is provided to measure the ambient acoustic environment, and an error microphone is included to measure the ambient audio and transducer output at the transducer, thus giving an indication of the effectiveness of the noise cancelation. A secondary path estimating adaptive filter is used to remove the playback audio from the error microphone signal, in order to generate an error signal. However, depending on the presence (and level) of the audio signal reproduced by the personal audio device, e.g., downlink audio during a telephone conversation or playback audio from a media file/connection, the secondary path adaptive filter may not be able to continue to adapt to estimate the secondary path. Therefore, the present invention uses injected noise to provide enough energy for the secondary path estimating adaptive filter to continue to adapt, while remaining at a level that is unnoticeable to the listener.

Figure 1:
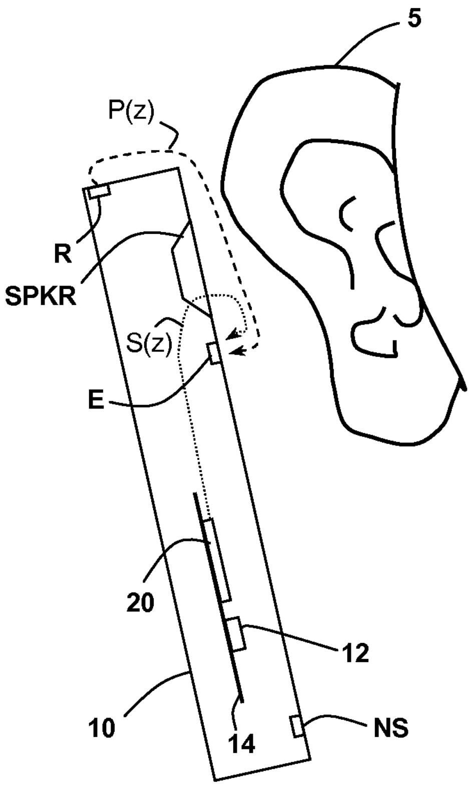
FIG. 1 is an illustration of a wireless telephone 10 in accordance with an embodiment of the present invention.

Referring now to FIG. 1, a wireless telephone 10 is illustrated in accordance with an embodiment of the present invention is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer such as speaker SPKR that reproduces distant speech received by wireless telephone 10, along with other local audio event such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment and is positioned away from the typical position of a user's mouth, so that the near-end speech is minimized in the signal produced by reference microphone R. A third microphone, error microphone E, is provided in order to further improve the ANC operation by providing a measure of the ambient audio combined with the audio reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS, and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events present at error microphone E. Since acoustic path P(z) extends from reference microphone R to error microphone E, the ANC circuits are essentially estimating acoustic path P(z) combined with removing effects of an electro-acoustic path S(z). Electro-acoustic path S(z) represents the response of the audio output circuits of CODEC IC 20 and the acoustic/electric transfer function of speaker SPKR including the coupling between speaker SPKR and error microphone E in the particular acoustic environment. S(z) is affected by the proximity and structure of ear 5 and other physical objects and human head structures that may be in proximity to wireless telephone 10, when wireless telephone is not firmly pressed to ear 5. While the illustrated wireless telephone 10 includes a two microphone ANC system with a third near speech microphone NS, some aspects of the present invention may be practiced in a system in accordance with other embodiments of the invention that do not include separate error and reference microphones, or yet other embodiments of the invention in which a wireless telephone uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention.

Figure 2:
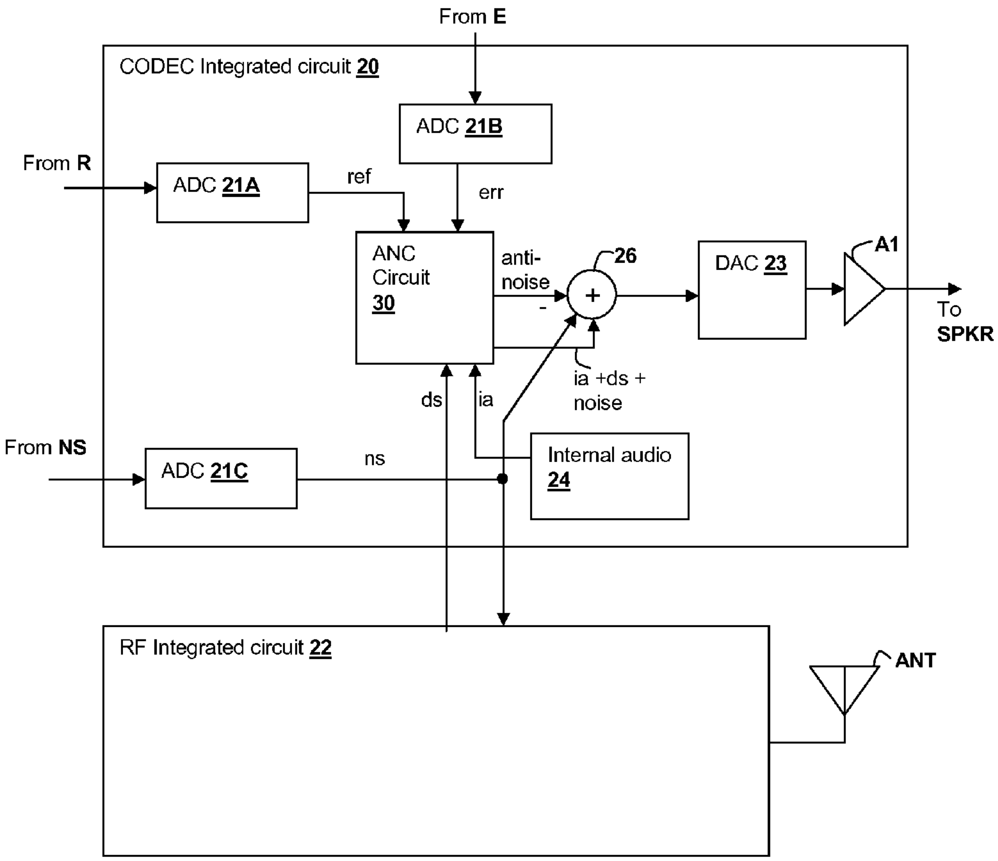
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals ia from internal audio sources 24, the anti-noise signal anti-noise generated by ANC circuit 30, which by convention has the same polarity as the noise in reference microphone signal ref and is therefore subtracted by combiner 26, a portion of near speech signal ns so that the user of wireless telephone 10 hears their own voice in proper relation to downlink speech ds, which is received from radio frequency (RF) integrated circuit 22. In accordance with an embodiment of the present invention, downlink speech ds is provided to ANC circuit 30, which, when both downlink speech ds and internal audio ia are absent or low in amplitude, adds noise to the combined source audio signal including downlink speech ds and internal audio ia or replaces source audio (ds+ia) with an injected noise signal. The downlink speech ds, internal audio ia, and noise (or source audio/noise if applied as alternative signals) are provided to combiner 26, so that signal (ds+ia+noise) is always present to estimate acoustic path P(z) with a secondary path adaptive filter within ANC circuit 30. Near speech signal ns is also provided to RF integrated circuit 22 and is transmitted as uplink speech to the service provider via antenna ANT.

Figure 3:
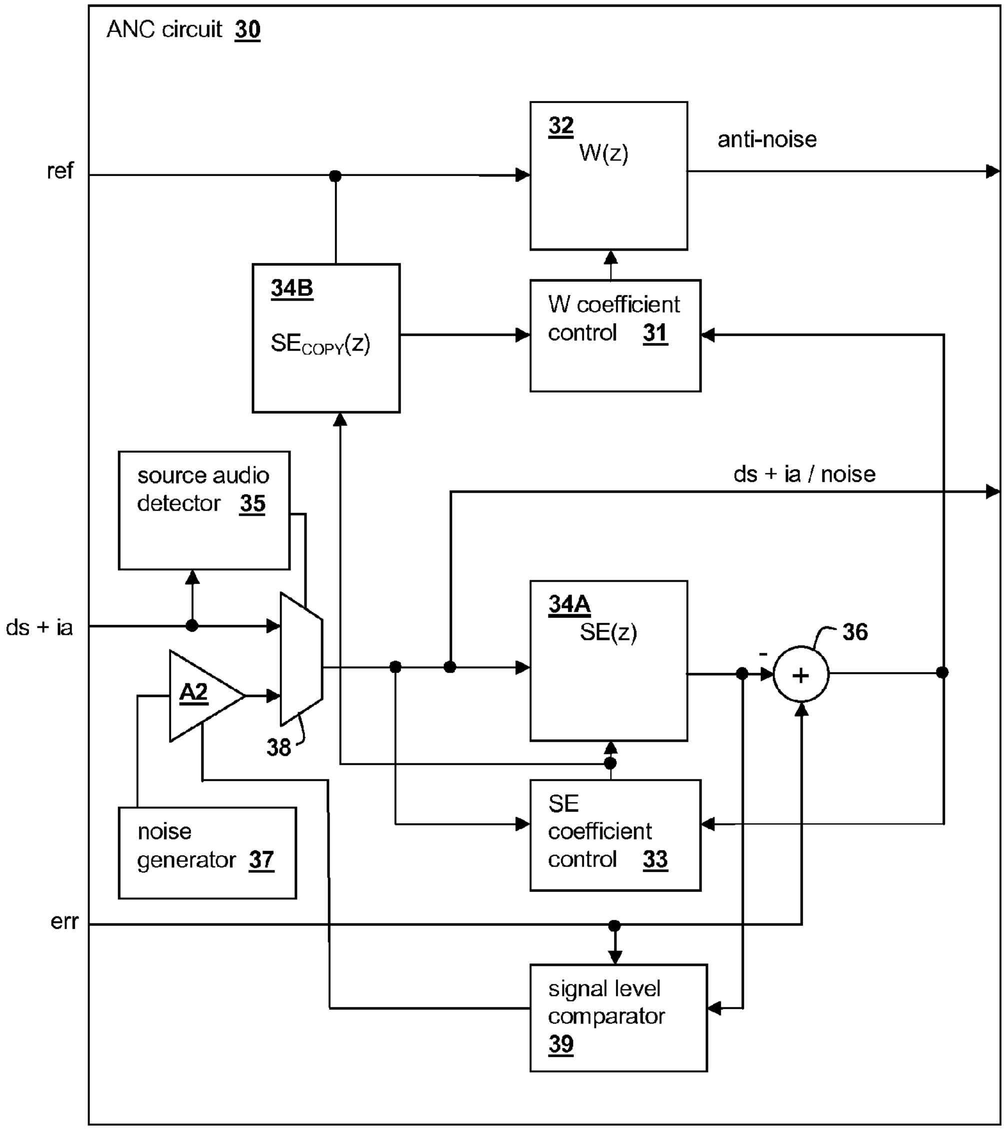
FIG. 3 is a block diagram depicting signal processing circuits and functional blocks within ANC circuit 30 of CODEC integrated circuit 20 of FIG. 2 in accordance with an embodiment of the present invention.

Referring now to FIG. 3, details of ANC circuit 30 are shown in accordance with an embodiment of the present invention. An adaptive filter 32 receives reference microphone signal ref and under ideal circumstances, adapts its transfer function W(z) to be P(z)/S(z) to generate the anti-noise signal anti-noise, which is provided to an output combiner that combines the anti-noise signal with the audio to be reproduced by the transducer, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err. The signals processed by W coefficient control block 31 are the reference microphone signal ref as shaped by a copy of an estimate of the response of path S(z) provided by filter 34B and another signal that includes error microphone signal err. By transforming reference microphone signal ref with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z). In addition to error microphone signal err, the other signal processed along with the output of filter 34B by W coefficient control block 31 includes an inverted amount of the source audio including downlink audio signal ds and internal audio ia that has been processed by filter response SE(z), of which response $SE_{COPY}(z)$ is a copy. By injecting an inverted amount of source audio, adaptive filter 32 is prevented from adapting to the relatively large amount of source audio present in error microphone signal err and by transforming the inverted copy of downlink audio signal ds and internal audio ia with the estimate of the response of path S(z), the source audio that is removed from error microphone signal err before processing should match the expected version of downlink audio signal ds, and internal audio ia reproduced at error microphone signal err, since the electrical and acoustical path of S(z) is the path taken by downlink audio signal ds and internal audio ia to arrive at error microphone E. Filter 34B is not an adaptive filter, per se, but has an adjustable response that is tuned to match the response of adaptive filter 34A, so that the response of filter 34B tracks the adapting of adaptive filter 34A.

To implement the above, adaptive filter 34A has coefficients controlled by SE coefficient control block 33, which processes the source audio (ds+ia) and error microphone signal err after removal, by a combiner 36, of the above-described filtered downlink audio signal ds and internal audio ia, that has been filtered by adaptive filter 34A to represent the expected source audio delivered to error microphone E. Adaptive filter 34A is thereby adapted to generate a signal from downlink audio signal ds and internal audio ia, that when subtracted from error microphone signal err, contains the content of error microphone signal err that is not due to source audio (ds+ia). However, if downlink audio signal ds and internal audio ia are both absent, or have very low amplitude, SE coefficient control block 33 will not have sufficient input to estimate acoustic path S(z). Therefore, in ANC circuit 30, a source audio detector 35, which detects whether sufficient source audio (ds+ia) is present, and updates the secondary path estimate if sufficient source audio (ds+ia) is present. Source audio detector 35 may be replaced by a speech presence signal if such is available from a digital source of the downlink audio signal ds, or a playback active signal provided from media playback control circuits. A selector 38 selects the output of a noise generator 37 if source audio (ds+ia) is absent or low in amplitude, which provides output ds+ia/noise to combiner 26 of FIG. 2, and an input to secondary path adaptive filter 34A and SE coefficient control block 33, allowing ANC circuit 30 to maintain estimating acoustic path S(z). Alternatively, selector 38 can be replaced with a combiner that adds the noise signal to source audio (ds+ia).

When source audio (ds+ia) is absent, speaker SPKR of FIG. 1 will actually reproduce noise injected from noise generator 37, thus it would be undesirable for the user of the device to hear the injected noise. Therefore, ANC circuit 30 includes a signal level comparator 39 that compares the output of secondary path adaptive filter 34A with error microphone signal err. The output of secondary path adaptive filter 34A provides a good estimate of the downlink speech ds or injected noise that the user actually hears, since acoustic path S(z) that is estimated by secondary path adaptive filter 34A is the path from the speaker SPKR to error microphone E. Error microphone signal err is then used to determine a comparison threshold, since error microphone signal err is a measure of the total energy heard by the user. As an alternative, predetermined or other dynamic thresholds may be used, such as thresholds determined from the reference microphone signal ref or near speech signal ns. A criteria such as maintaining the level of the output of secondary path adaptive filter 34A at 20 dB below the corresponding normalized level of error microphone signal err can be used to either adjust the gain of the output of noise generator 37 using gain control A2, or to further condition the selection of the output of noise generator

37 by selector 38 so that noise injection is stopped when the amplitude of the output of secondary path adaptive filter 34A becomes too great relative to error microphone signal err. The amplitude of the output of secondary path adaptive filter 34A and error microphone signal err can be determined by techniques such as least-mean-squares, squarers, absolute value peak detectors or decimators. The following control equation can be used to adjust the gain applied to the injected noise:

$$\text{gain}(i)=\text{gain}(i-1)+(\text{mag}(\text{err})/\text{atten}-\text{mag}(\text{seout}))$$

where i is the step interval, atten is the desired ratio of the amplitude of the error signal to the noise (desired attenuation, e.g., 20 dB), ampl(err) is the magnitude of the error signal and mag(seout) is the magnitude of the output of the secondary path adaptive filter 34A.

Figure 4:
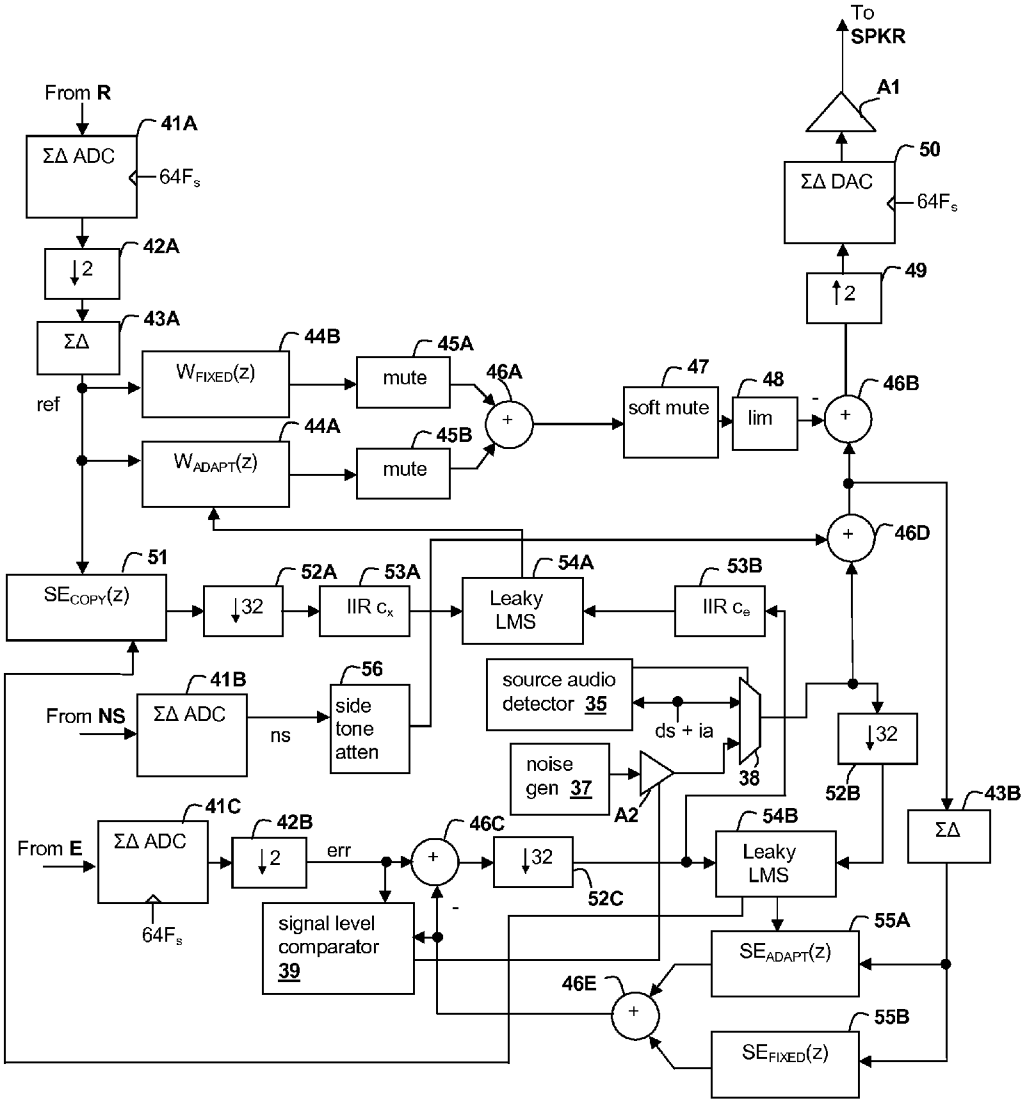
FIG. 4 is a block diagram depicting signal processing circuits and functional blocks within an integrated circuit in accordance with an embodiment of the present invention.

Referring now to FIG. 4, a block diagram of an ANC system is shown for illustrating ANC techniques in accordance with an embodiment of the invention, as may be implemented within CODEC integrated circuit 20. Reference microphone signal ref is generated by a delta-sigma ADC 41A that operates at 64 times oversampling and the output of which is decimated by a factor of two by a decimator 42A to yield a 32 times oversampled signal. A delta-sigma shaper 43A spreads the energy of images outside of bands in which a resultant response of a parallel pair of filter stages 44A and 44B will have significant response. Filter stage 44B has a fixed response $W_{FIXED}(z)$ that is generally predetermined to provide a starting point at the estimate of P(z)/S(z) for the particular design of wireless telephone 10 for a typical user. An adaptive portion $W_{ADAPT}(z)$ of the response of the estimate of P(z)/S(z) is provided by adaptive filter stage 44A, which is controlled by a leaky least-means-squared (LMS) coefficient controller 54A. Leaky LMS coefficient controller MA is leaky in that the response normalizes to flat or otherwise predetermined response over time when no error input is provided to cause leaky LMS coefficient controller 54A to adapt. Providing a leaky controller prevents long-term instabilities that might arise under certain environmental conditions, and in general makes the system more robust against particular sensitivities of the ANC response.

In the system depicted in FIG. 4, the reference microphone signal is filtered by a copy $SE_{COPY}(z)$ of the estimate of the response of path S(z), by a filter 51 that has a response $SE_{COPY}(z)$, the output of which is decimated by a factor of 32 by a decimator 52A to yield a baseband audio signal that is provided, through an infinite impulse response (IIR) filter 53A to leaky LMS 54A. Filter 51 is not an adaptive filter, per se, but has an adjustable response that is tuned to match the combined response of filter stages 55A and 55B, so that the response of filter 51 tracks the adapting of response SE(z). The error microphone signal err is generated by a delta-sigma ADC 41C that operates at 64 times oversampling and the output of which is decimated by a factor of two by a decimator 42B to yield a 32 times oversampled signal. As in the system of FIG. 3, an amount of source audio (ds+ia) that has been filtered by an adaptive filter to apply response S(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. Response S(z) is produced by another parallel set of filter stages 55A and 55B, one of which, filter stage 55B has fixed response $SE_{FIXED}(z)$, and the other of which, filter stage 55A has an adaptive response $SE_{ADAPT}(z)$ controlled by leaky LMS coefficient controller MB. The outputs of filter stages 55A and 55B are combined by a combiner 46E. Similar to the implementation of filter response W(z) described above, response $SE_{FIXED}(z)$ is generally a predetermined response known to provide a suitable starting point under various operating conditions for electrical/acoustical path S(z). Filter 51 is a copy of adaptive filter 55A/55B, but is not itself an adaptive filter, i.e., filter 51 does not separately adapt in response to its own output, and filter 51 can be implemented using a single stage or a dual stage. A separate control value is provided in the system of FIG. 4 to control the response of filter 51, which is shown as a single adaptive filter stage. However, filter 51 could alternatively be implemented using two parallel stages and the same control value used to control adaptive filter stage 55A could then be used to control the adjustable filter portion in the implementation of filter 51.

As in ANC circuit 30 of FIG. 3, the input to filter stages 55A and 55B has a component selected from source audio (ds+ia) or the output of noise generator 37 with gain controlled by gain control A2, as selected by selector 38, the output of which is provided to the input of a combiner 46D that adds a portion of near-end microphone signal ns that has been generated by sigma-delta ADC 41B and filtered by a sidetone attenuator 56 to prevent feedback conditions. The output of combiner 46D is shaped by a sigma-delta shaper 43B that provides inputs to filter stages 55A and 55B that has been shaped to shift images outside of bands where filter stages 55A and 55B will have significant response. Signal level comparator 39 compares the output of combiner 46E, which is the output of the secondary path adaptive filter formed by filter stages 55A and 55B, and error microphone signal err and controls the gain applied to the output of noise generator 37 via gain control A2 in conformity with a result of the comparison. Speech detector 35 controls whether selector selects source audio (ds+ia) or the output of gain control A2 as in ANC circuit 30 of FIG. 3. The inputs to leaky LMS control block 54B are also at baseband, provided by decimating a combination of the selected source audio/noise, provided by selector 38, by a decimator 52B that decimates by a factor of 32, and another input is provided by decimating the output of a combiner 46C that has removed the signal generated from the combined outputs of adaptive filter stage 55A and filter stage 55B that are combined by another combiner 46E from error microphone signal err. As mentioned above, selector 38 can alternatively be replaced by a combiner that combines the noise signal with source audio (ds+ia). The output of combiner 46C represents error microphone signal err with the components due to source audio (ds+ia) removed, which is provided to LMS control block 54B after decimation by decimator 52C. The other input to LMS control block 54B is the baseband signal produced by decimator 52B. The above arrangement of baseband and oversampled signaling provides for simplified control and reduced power consumed in the adaptive control blocks, such as leaky LMS controllers MA and 54B, while providing the tap flexibility afforded by implementing adaptive filter stages 44A-44B, 55A-55B and filter 51 at the oversampled rates.

In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64*x* oversampling rate. The output of DAC 50 is provided to amplifier A1, which generates the signal delivered to speaker SPKR.

Each or some of the elements in the system of FIG. 4, as well in as the exemplary circuits of FIG. 2 and FIG. 3, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected changes in ear pressure as described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a first combiner for combining a source audio signal containing the source audio and the anti-noise signal to provide an output signal for reproduction by the transducer;

a reference microphone mounted on the housing for providing a reference microphone signal indicative of the ambient audio sounds;

an error microphone mounted on the housing in proximity to the transducer for providing an error microphone signal indicative of the acoustic output of the transducer and the ambient audio sounds at the transducer;

a controllable noise source for providing a noise signal;

a source audio detector having an input coupled to the source audio signal for determining whether source audio of sufficient amplitude is present in the source audio signal; and a processing circuit that generates the anti-noise signal from the reference microphone signal to reduce the presence of the ambient audio sounds heard by the listener in conformity with an error signal and the reference microphone signal, wherein the processing circuit implements a secondary path adaptive filter having a secondary path response that shapes the source audio to generate shaped source audio and a second combiner that removes the shaped source audio from the error microphone signal to provide the error signal, and wherein the processing circuit, in response to the source audio detector determining that source audio of sufficient amplitude is not present in the source audio signal, selectively injects noise from the controllable noise source into the secondary path adaptive filter and further injects the noise into the first combiner in place of or in combination with the source audio signal to cause the secondary path adaptive filter to continue to adapt when the source audio is absent or has reduced amplitude, and wherein the processing circuit further controls the controllable noise source in conformity with an output of the secondary path adaptive filter.

2. The personal audio device of claim 1, wherein the processing circuit measures an amplitude of the output of the secondary path adaptive filter and changes the controllable noise source if the amplitude of the output of the secondary path adaptive filter exceeds a threshold amplitude.

3. The personal audio device of claim 2, wherein the processing circuit adjusts a gain applied to the noise signal if the amplitude of the output of the secondary path adaptive filter exceeds the threshold amplitude.

4. The personal audio device of claim 2, wherein the processing circuit disables injection of the noise signal if the amplitude of the output of the secondary path adaptive filter exceeds the threshold amplitude.

5. The personal audio device of claim 2, wherein the processing circuit further determines the threshold amplitude from an amplitude of the error signal, wherein the threshold amplitude is dynamically adjusted according to the amplitude of the error signal.

6. The personal audio device of claim 5, wherein the threshold amplitude is a level 20 dB below the amplitude of the error signal.

7. The personal audio device of claim 1, wherein the processing circuit detects that an amplitude of the source audio is below a threshold amplitude and only changes the controllable noise source if the amplitude of the source audio is below the threshold amplitude.

8. The personal audio device of claim 1, wherein the processing circuit implements an adaptive filter having a response that generates the anti-noise signal from the reference signal to reduce the presence of the ambient audio sounds heard by the listener, wherein the processing circuit shapes the response of the adaptive filter in conformity with the error signal and the reference microphone signal.

9. A method of canceling ambient audio sounds in the proximity of a transducer of a personal audio device, the method comprising:

first measuring ambient audio sounds with a reference microphone to produce a reference microphone signal;

second measuring an output of the transducer and the ambient audio sounds at the transducer with an error microphone;

adaptively generating an anti-noise signal from a result of the first measuring and the second measuring for countering the effects of ambient audio sounds at an acoustic output of the transducer;

combining the anti-noise signal with a source audio signal to generate an audio signal provided to the transducer;

shaping a copy of the source audio with a secondary path response to generate shaped source audio;

removing the result of the shaping the copy of the source audio from the error microphone signal to produce an error signal indicative of the combined anti-noise and ambient audio sounds delivered to the listener;

generating a noise signal;

determining whether source audio of sufficient amplitude is present in the source audio signal using a source audio detector having an input coupled to the source audio signal;

selectively, in response to determining that source audio of sufficient amplitude is not present, injecting the noise signal into the secondary path adaptive filter in place of or in combination with the source audio signal and wherein the combining further combines the noise in place of or in combination with the source audio signal to cause the secondary path adaptive filter to continue to adapt when the source audio is absent or has reduced amplitude; and controlling the controllable noise source in conformity with an output of the secondary path adaptive filter.

10. The method of claim 9, further comprising measuring an amplitude of the output of the secondary path adaptive filter, wherein the controlling the controllable noise source adjusts the controllable noise source if the amplitude of the output of the secondary path adaptive filter exceeds a threshold amplitude.

11. The method of claim 10, wherein the controlling the controllable noise source adjusts a gain applied to the noise signal if the amplitude of the output of the secondary path adaptive filter exceeds the threshold amplitude.

12. The method of claim 10, wherein the controlling the controllable noise source disables injection of the noise signal if the amplitude of the output of the secondary path adaptive filter exceeds the threshold amplitude.

13. The method of claim 10, further comprising determining the threshold amplitude from an amplitude of the error signal, wherein the threshold amplitude is dynamically adjusted according to the amplitude of the error signal.

14. The method of claim 13, wherein the threshold amplitude is a level 20 dB below the amplitude of the error signal.

15. The method of claim 9, further comprising detecting that an amplitude of the source audio is below a threshold amplitude, and wherein the controlling the controllable noise source only changes the controllable noise source if the amplitude of the source audio is below the threshold amplitude.

16. The method of claim 9, wherein the adaptively generating adapts a response of an adaptive filter that filters an output of the reference microphone to generate the anti-noise signal to reduce the presence of the ambient audio sounds heard by the listener, wherein the adaptively generating shapes the response of the adaptive filter in conformity with the error signal and the reference microphone signal.

17. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a first combiner for combining a source audio signal containing the source audio and the anti-noise signal to provide an output signal for reproduction by the transducer;

a reference microphone input for receiving a reference microphone signal indicative of the ambient audio sounds;

an error microphone input for receiving an error microphone signal indicative of the acoustic output of the transducer and the ambient audio sounds at the transducer;

a controllable noise source for providing a noise signal;

a source audio detector having an input coupled to the source audio signal for determining whether source audio of sufficient amplitude is present in the source audio signal; and a processing circuit that generates the anti-noise signal from the reference microphone signal to reduce the presence of the ambient audio sounds heard by the listener in conformity with an error signal and the reference microphone signal, wherein the processing circuit implements a secondary path adaptive filter having a secondary path response that shapes the source audio to generate shaped source audio and a second combiner that removes the shaped source audio from the error microphone signal to provide the error signal, and wherein the processing circuit, in response to the source audio detector determining that source audio of sufficient amplitude is not present in the source audio signal, selectively injects noise from the controllable noise source into the secondary path adaptive filter and further injects the noise into the first combiner in place of or in combination with the source audio signal to cause the secondary path adaptive filter to continue to adapt when the source audio is absent or has reduced amplitude, and wherein the processing circuit further controls the controllable noise source in conformity with an output of the secondary path adaptive filter.

18. The integrated circuit of claim 17, wherein the processing circuit measures an amplitude of the output of the secondary path adaptive filter and changes the controllable noise source if the amplitude of the output of the secondary path adaptive filter exceeds a threshold amplitude.

19. The integrated circuit of claim 18, wherein the processing circuit adjusts a gain applied to the noise signal if the amplitude of the output of the secondary path adaptive filter exceeds the threshold amplitude.

20. The integrated circuit of claim 18, wherein the processing circuit disables injection of the noise signal if the amplitude of the output of the secondary path adaptive filter exceeds the threshold amplitude.

21. The integrated circuit of claim 18, wherein the processing circuit further determines the threshold amplitude from an amplitude of the error signal, wherein the threshold amplitude is dynamically adjusted according to the amplitude of the error signal.

22. The integrated circuit of claim 21, wherein the threshold amplitude is a level 20 dB below the amplitude of the error signal.

23. The integrated circuit of claim 17, wherein the processing circuit detects that an amplitude of the source audio is below a threshold amplitude and only changes the controllable noise source if the amplitude of the source audio is below the threshold amplitude.

24. The integrated circuit of claim 17, wherein the processing circuit implements an adaptive filter having a response that generates the anti-noise signal from the reference signal to reduce the presence of the ambient audio sounds heard by the listener, wherein the processing circuit shapes the response of the adaptive filter in conformity with the error signal and the reference microphone signal.

* * * * *